United States Patent
Kwon et al.

(10) Patent No.: US 9,165,349 B2
(45) Date of Patent: Oct. 20, 2015

(54) APPARATUS FOR GENERATING DIAGNOSIS IMAGE, MEDICAL IMAGING SYSTEM, AND METHOD FOR PROCESSING IMAGE

(75) Inventors: Jae-hyun Kwon, Hwaseong-si (KR); Young-hun Sung, Hwaseong-si (KR); Sung-su Kim, Yongin-si (KR); Hyun-hwa Oh, Hwaseong-si (KR)

(73) Assignee: Samsung Electronics Co., Ltd., Suwon-si (KR)

(*) Notice: Subject to any disclaimer, the term of this patent is extended or adjusted under 35 U.S.C. 154(b) by 222 days.

(21) Appl. No.: 13/554,638

(22) Filed: Jul. 20, 2012

(65) Prior Publication Data

US 2013/0022259 A1    Jan. 24, 2013

(30) Foreign Application Priority Data

Jul. 22, 2011    (KR) ........................ 10-2011-0073283

(51) Int. Cl.
*A61B 6/00* (2006.01)
*G06T 5/00* (2006.01)
*G06T 5/50* (2006.01)

(52) U.S. Cl.
CPC .................. *G06T 5/009* (2013.01); *A61B 6/482* (2013.01); *G06T 5/50* (2013.01); *G06T 2207/10116* (2013.01); *G06T 2207/20028* (2013.01); *G06T 2207/20221* (2013.01); *G06T 2207/30068* (2013.01)

(58) Field of Classification Search
CPC ............. G06T 5/002; G06T 2207/30004; G06T 2207/10116; G06T 2207/10081; G06T 2207/20192; G06T 2207/20221; A61B 6/482; A61B 6/466

USPC ................................................... 382/131, 132
See application file for complete search history.

(56) References Cited

U.S. PATENT DOCUMENTS

| | | | |
|---|---|---|---|
| 7,856,134 B2 | 12/2010 | Rührnschopf et al. | |
| 8,611,633 B2 * | 12/2013 | Kwon et al. | 382/132 |
| 2008/0279440 A1 * | 11/2008 | Couwenhoven et al. | 382/132 |
| 2009/0185733 A1 | 7/2009 | Heinlein et al. | |
| 2010/0278407 A1 * | 11/2010 | Dzyubak et al. | 382/131 |
| 2010/0278411 A1 * | 11/2010 | Krauss et al. | 382/131 |
| 2012/0063662 A1 | 3/2012 | Kwon et al. | |

FOREIGN PATENT DOCUMENTS

| | | |
|---|---|---|
| JP | 2007-44275 A | 2/2007 |
| KR | 10-2010-0040652 A | 4/2010 |
| KR | 10-2011-0024600 A | 3/2011 |
| KR | 10-2012-0028760 A | 3/2012 |

* cited by examiner

*Primary Examiner* — Vu Le
*Assistant Examiner* — Kenny Cese
(74) *Attorney, Agent, or Firm* — NSIP Law

(57) ABSTRACT

An apparatus for generating a diagnosis image includes a local contrast characteristic calculator configured to calculate local contrast characteristics of radiation image data of a low-energy sub-band from radiation image data generated by radiation having at least two energy bands passing through a subject; a local contrast characteristic applier configured to apply the calculated local contrast characteristics to radiation image data of a full-energy band generated by the radiation having at least two energy bands passing through the subject; and a diagnosis image generator configured to generate a diagnosis image of the subject based on the radiation image data of the full-energy band to which the local contrast characteristics have been applied.

20 Claims, 5 Drawing Sheets

APPARATUS FOR GENERATING DIAGNOSIS IMAGE, MEDICAL IMAGING SYSTEM, AND METHOD FOR PROCESSING IMAGE

CROSS-REFERENCE TO RELATED APPLICATIONS

This application claims the benefit of Korean Patent Application No. 10-2011-0073283 filed on Jul. 22, 2011, in the Korean Intellectual Property Office, the disclosure of which is incorporated herein by reference in its entirety.

BACKGROUND

1. Field

This disclosure relates to an apparatus for generating a diagnosis image, a medical imaging system, and a method of processing an image.

2. Description of the Related Art

A medical imaging system using radiation, such as an x-ray, obtains a radiation image by radiating and penetrating a subject, such as a human body, with an x-ray. The medical imaging system may generate a diagnosis image of the subject based on a difference between attenuation characteristics according to energy bands of different tissues of the subject.

SUMMARY

According to an aspect, an apparatus for generating a diagnosis image includes a local contrast characteristic calculator configured to calculate local contrast characteristics of radiation image data of a low-energy sub-band from radiation image data generated by radiation having at least two energy bands passing through a subject; a local contrast characteristic applier configured to apply the calculated local contrast characteristics to radiation image data of a full-energy band generated by the radiation having at least two energy bands passing through the subject; and a diagnosis image generator configured to generate a diagnosis image of the subject based on the radiation image data of the full-energy band to which the calculated local contrast characteristics have been applied.

The local contrast characteristics may be a local contrast gain of the radiation image data of the low-energy sub-band.

The local contrast characteristic calculator may be further configured to calculate the local contrast characteristics based on the radiation image data of the low-energy sub-band and filtered radiation image data obtained by passing the radiation image data of the low-energy sub-band through a low-pass filter (LPF).

The local contrast characteristic calculator may be further configured to adjust a resolution improvement degree of the diagnosis image generated by the diagnosis image generator by adjusting parameters of the LPF.

The passing of the radiation image data of the low-energy sub-band through the LPF to obtain the filtered radiation image data may include passing the radiation image data of the low-energy sub-band through a bilateral filter, or a Gaussian filter, or an averaging filter, or performing wavelet transformation, or curvelet transformation, or contourlet transformation on the radiation image data of the low-energy sub-band.

The passing of the radiation image data of the low-energy sub-band through the LPF to obtain the filtered radiation image data may include passing the radiation image data of the low-energy sub-band through a Gaussian filter or a bilateral filter; and the local contrast characteristic calculator may be further configured to adjust a contrast improvement degree of the diagnosis image generated by the diagnosis image generator by adjusting a standard deviation of the Gaussian filter or an intensity level parameter of the bilateral filter.

The local contrast characteristic applier may be further configured to apply the calculated local contrast characteristics to filtered radiation image data obtained by passing the radiation image data of the full-energy band through a low-pass filter (LPF).

The LPF may be a bilateral filter, or a Gaussian filter, or an averaging filter.

The diagnosis image generator may be further configured to adjust a resolution improvement degree of the diagnosis image by combining the radiation image data of the full-energy band to which the calculated local contrast characteristics have not been applied with the radiation image data of the full-energy band to which the calculated local contrast characteristics have been applied according to a resolution improvement weight.

The apparatus may further include a data processor configured to divide the radiation image data of the low-energy sub-band into a plurality of brightness regions based on a brightness reference point; and perform contrast stretching on the radiation image data of the low-energy sub-band by performing a first contrast stretching technique on radiation image data of the low-energy sub-band having a brightness level below the brightness reference point, and performing a second contrast stretching technique different from the first contrast stretching technique on radiation image data of the low-energy sub-band having a brightness level equal to or above the brightness reference point; wherein the local contrast characteristic calculator may be further configured to calculate the local contrast characteristics based on the radiation image data of the low-energy sub-band on which the contrast stretching has been performed.

According to an aspect, a medical imaging system includes an apparatus configured to generate a diagnosis image of a subject by applying local contrast characteristics of radiation image data of a low-energy sub-band to radiation image data of a full-energy band, the radiation image data of the low-energy sub-band and the radiation image data of the full-energy band having been generated by radiation passing through the subject; and a display unit configured to display the generated diagnosis image.

The local contrast characteristics may be a local contrast gain of the radiation image data of the low-energy sub-band.

The apparatus may be further configured to calculate the local contrast characteristics based on the radiation image data of the low-energy sub-band and filtered radiation image data obtained by passing the radiation image data of the low-energy sub-band through a low-pass filter (LPF).

According to an aspect, a method of processing an image includes generating radiation image data of a low-energy sub-band from radiation image data generated by radiation having at least two energy bands passing through a subject; calculating local contrast characteristics of the generated radiation image data of the low-energy sub-band; and applying the calculated local contrast characteristics to radiation image data of a full-energy band.

The local contrast characteristics may be a local contrast gain of the radiation image data of the low-energy sub-band.

The calculating of the local contrast characteristics may include calculating the local contrast characteristics based on the radiation image data of the low-energy sub-band and filtered radiation data obtained by passing the radiation image data of the low-energy sub-band through a low-pass filter (LPF).

The LPF may be a bilateral filter, or a Gaussian filter, or an averaging filter.

The method may further include dividing the radiation image data of the low-energy sub-band into a plurality of brightness regions based on a brightness reference point; and performing contrast stretching on the radiation image data of the low-energy sub-band by performing a first contrast stretching technique on radiation image data of the low-energy sub-band having a brightness level lower than the brightness reference point, and performing a second contrast stretching technique different from the first contrast stretching technique on radiation image data of the low-energy sub-band having a brightness level equal to or above the brightness reference point; wherein the calculating of the local contrast characteristics may include calculating the local contrast characteristics based on the radiation image data of the low-energy sub-band on which the contrast stretching has been performed.

The method may further include generating a diagnosis image of the subject by combining the radiation image data of the full-energy band to which the calculated local contrast characteristics have not been applied with the radiation image data of the full-energy band to which the local contrast characteristics have been applied according to a resolution improvement weight.

According to an aspect, a non-transitory computer-readable storage medium stores program instructions for controlling one or more processors to perform the method described above.

According to an aspect, an apparatus for generating a diagnosis image includes a local contrast characteristic calculator configured to calculate local contrast characteristics of radiation image data of a first energy band from radiation image data that was generated by radiation passing through a subject; a local contrast characteristic applier configured to apply the calculated local contrast characteristics to radiation image data of a second energy band wider than the first energy band that was generated by the radiation passing through the subject; and a diagnosis image generator configured generate a diagnosis image of the subject based on the radiation image data of the second energy band to which the local contrast characteristics have been applied.

The first energy band may include energies not exceeding a predetermined energy; and the second energy band may include the first energy band and energies above the predetermined energy, and does not include any energy lower than a lowest energy of the first energy band.

The first energy band may be a lowest energy band of the radiation that has passed through the subject; the second energy band may include the first energy band; and the radiation that has passed through the subject may include radiation in a third energy band including the second energy band.

Additional aspects will be set forth in part in the description that follows and, in part, will be apparent from the description, or may be learned by practice of the described examples.

BRIEF DESCRIPTION OF THE DRAWINGS

The above and other aspects will become apparent and more readily appreciated from the following description of examples, taken in conjunction with the accompanying drawings of which.

DETAILED DESCRIPTION

Figure 1:
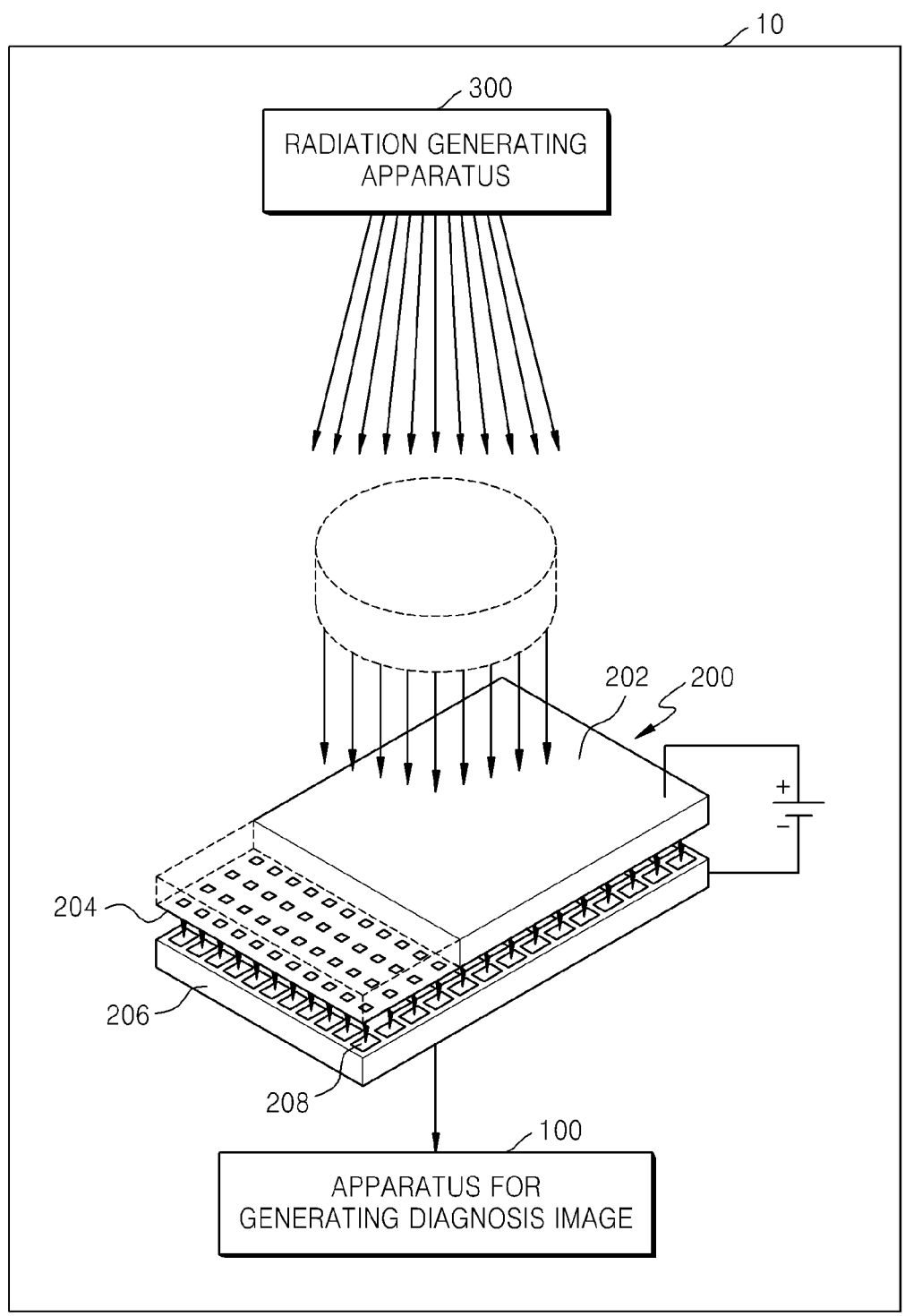
FIG. 1 is a diagram of a radiation image capturing system according to an example.

Reference will now be made in detail to examples that are illustrated in the accompanying drawings, wherein like reference numerals refer to like elements throughout.

FIG. 1 is a diagram of a radiation image capturing system 10 according to an example. Referring to FIG. 1, the radiation image capturing system 10 includes an apparatus 100 for generating a diagnosis image, a detector 200, and a radiation generating apparatus 300. In FIG. 1, the detector 200 and the apparatus 100 are shown as individual devices, but alternatively, the detector 200 and the apparatus 100 may be implemented as one device having functions of both the detector 200 and the apparatus 100.

Only elements relevant to this example are shown in the radiation image capturing system 10 of FIG. 1. However, it will be apparent to one of ordinary skill in the art that other elements may also be included in the radiation image capturing system 10.

The apparatus 100 may be implemented by one or more processors. Each processor may be implemented as an array of a plurality of logic gates or as a combination of a general-use microprocessor and a memory storing a program executable in the microprocessor. Alternatively, the apparatus 100 may be implemented as one or more hardware components, or a combination of hardware and software components.

The radiation image capturing system 10 radiates radiation onto the subject, detects radiation that has passed through the subject, and generates a diagnosis image by performing predetermined processes on the detected radiation. Examples of the subject include breasts, bones, etc., of a human body, but are not limited thereto.

For example, the radiation image capturing system 10 may be a mammographic imaging system used to detect a lesion of breast tissues that are only formed of soft tissues, i.e., not bones, in a human body.

The radiation generating apparatus 300 generates radiation from a radiation source, and radiates the generated radiation onto the subject. The radiation may be an x-ray, but is not limited thereto. For example, the radiation radiated from the radiation generating apparatus 300 onto the subject may include either one or both of a multi-energy x-ray and a polychromatic x-ray.

The detector 200 generates radiation image data by detecting the radiation that has passed through the subject. In greater detail, the radiation image capturing system 10 generates the radiation image data by detecting the radiation that has passed through the subject from the radiation that was radiated from the radiation generating apparatus 300 onto the subject. The detector 200 may include a collimator having through holes for a beam having a predetermined size to penetrate therethrough.

When radiation, for example, x-rays, radiated onto the tissues forming the subject has different energy bands, degrees of radiation absorbed by each tissue are different for each energy band. By using such a characteristic, the radiation generating apparatus 300 and the detector 200 may obtain a plurality of pieces of radiation image data by radiating x-rays having at least two different energy bands onto the tissues, or may obtain a plurality of pieces of radiation image data reflecting attenuation characteristics according to each of at least two energy bands by using an energy discrimination detector.

The detector 200 is an energy discrimination detector. For convenience of description, the detector 200 in FIG. 1 is shown as a photon-counting detector (PCD) for detecting the radiation that has passed through the subject in each of a plurality of energy bands, but the detector 200 is not limited thereto.

Referring to FIG. 1, the PCD includes a semiconductor sensor chip 202, flip-chip bump bonding connections 204, and a complementary metal-oxide semiconductor (CMOS) pixel read-out chip 206. The CMOS pixel read-out chip 206 includes a plurality of single pixel read-out cells 208.

Accordingly, the PCD divides the radiation generated by the radiation generating apparatus 300 that has passed through the subject into at least two energy bands, detects the radiation in each of the at least two energy bands, and generates radiation image data of each energy band based on the detected radiation. The PCD and how to operate the PCD to divide radiation into at least two energy bands are well known to one of ordinary skill in the art, and thus will not be further described in detail here.

Also, the detector 200 may generate not only the radiation image data of each of the at least two energy bands, but may also generate radiation image data of a full-energy band of the radiation generated by the radiation generating apparatus 300 that has passed through the subject.

The generating of the radiation image data of each of the energy bands and the generating of the radiation image data of the full-energy band by the detector 200 will be described later with reference to FIGS. 2 and 3.

Accordingly, the detector 200 may generate a plurality of pieces of radiation image data having different information about the subject.

The apparatus 100 generates a diagnosis image of the subject by applying local contrast characteristics of radiation image data of a low-energy sub-band to the radiation image data of the full-energy band.

Accordingly, the radiation image capturing system 10 may provide a diagnosis image of the subject having an improved contrast.

Figure 2:
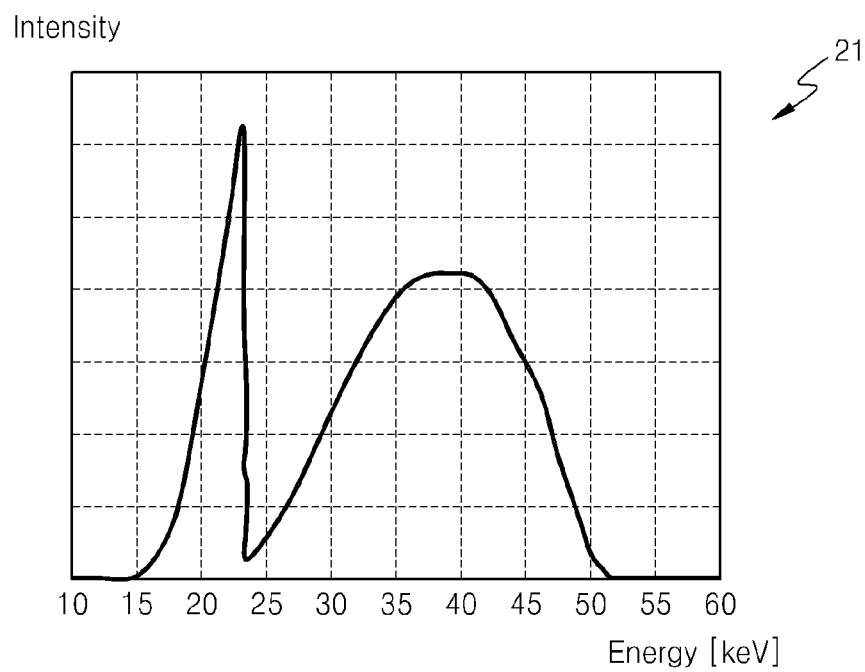
FIG. 2 is a graph of a spectrum of a full-energy band detected by a detector according to an example.

FIG. 2 is a graph 21 of a spectrum of a full-energy band detected by the detector 200 according to an example. Referring to FIGS. 1 and 2, the graph 21 shows intensity with respect to energy in the full-energy band of the radiation that has passed through the subject. The full-energy band is an energy band of the radiation radiated onto the subject by the radiation generating apparatus 300 that has passed through the subject.

The detector 200 detects an intensity of the full-energy band of the radiation that has passed through the subject, and generates the radiation image data of the full-energy band based on a result of the detection.

However, although the detector 200 in FIG. 2 generates the radiation image data of the full-energy band, if the detector 200 does not generate the radiation image data of the full-energy band, the radiation image data of the full-energy band may be generated based on radiation image data of each of a plurality of energy bands. This will be described in detail later with reference to FIG. 6.

Figure 3:
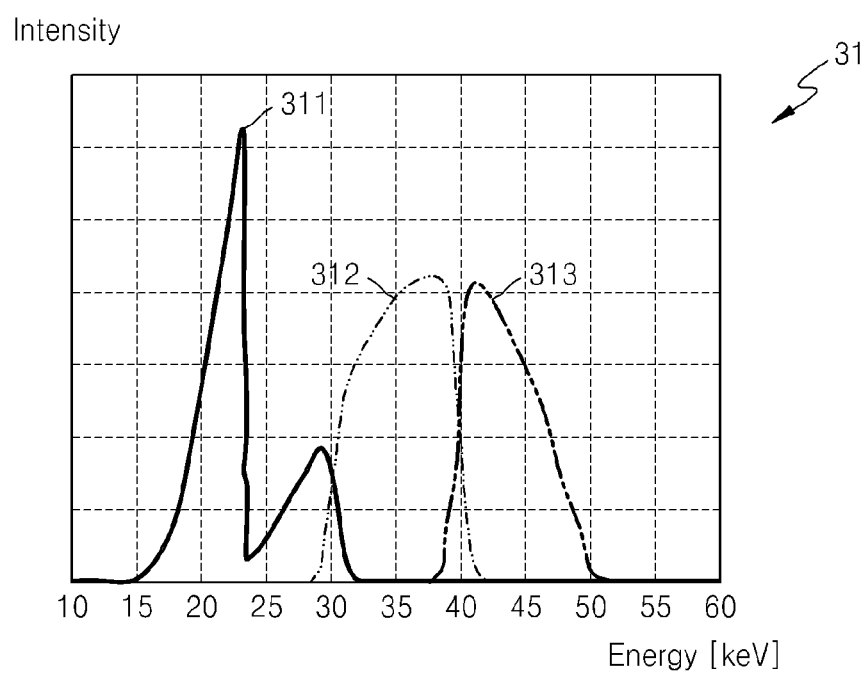
FIG. 3 is a graph of spectrums of three energy bands detected by a detector according to an example.

FIG. 3 is a graph 31 of spectrums of three energy bands detected by the detector 200 according to an example. Referring to FIGS. 1 and 3, the graph 31 shows intensity with respect to energy in each of the three energy bands of the radiation that has passed through the subject.

The three energy bands show that the radiation radiated onto the subject by the radiation generating apparatus 300 is divided into three energy bands. For example, the detector 200 divides the full-energy band into three sections, and generates radiation image data of each of the three energy bands.

Referring to FIG. 3, a first spectrum 311 shows intensity with respect to energy in a first energy band, a second spectrum 312 shows intensity with respect to energy in a second energy band, and a third spectrum 313 shows intensity with respect to energy in a third energy band.

Accordingly, the detector 200 detects the intensities of the three energy bands of the radiation that has passed through the subject, and generates radiation image data of each of the three energy bands according to a result of the detection.

In this case, the radiation image data of the first spectrum 311 may be radiation image data of a low-energy sub-band.

Although three energy bands are shown in FIG. 3, the number of energy bands is not limited to three, and the detector 200 may divide the full-energy band into at least two energy bands. Also, the detector 200 may suitably determine at least one energy level for dividing the full-energy band into at least two energy bands according to image capturing conditions and purposes.

Accordingly, the detector 200 generates the radiation image data of the low-energy sub-band, and outputs the generated radiation image data of the low-energy sub-band to the apparatus 100.

Figure 4:
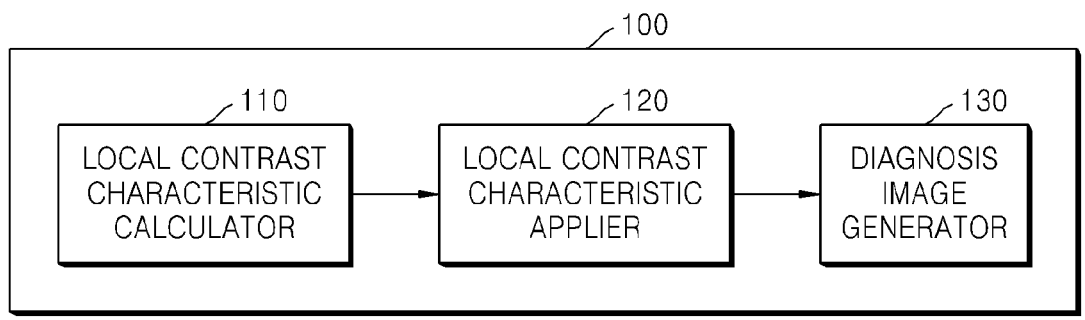
FIG. 4 is a block diagram of an apparatus for generating a diagnosis image according to an example.

FIG. 4 is a block diagram of the apparatus 100 for generating a diagnosis image according to an example. Referring to FIG. 4, the apparatus 100 includes a local contrast characteristic calculator 110, a local contrast characteristic applier 120, and a diagnosis image generator 130.

Only elements relevant to this example are shown in the apparatus 100 of FIG. 4. However, it will be apparent to one of ordinary skill in the art that other elements may also be included in the apparatus 100.

The local contrast characteristic calculator 110, the local contrast characteristic applier 120, and the diagnosis image generator 130 of FIG. 4 may be implemented by one or more processors. Each processor may be implemented as an array of a plurality of logic gates or as a combination of a general-use microprocessor and a memory storing a program executable in the microprocessor. Alternatively, the local contrast characteristic calculator 110, the local contrast characteristic applier 120, and the diagnosis image generator 130 may be implemented as one or more hardware components, or as a combination of hardware and software components.

The apparatus 100 generates a diagnosis image of the subject by applying the local contrast characteristics of the radiation image data of the low-energy sub-band to the radiation image data of the full-energy band.

The local contrast characteristic calculator 110 calculates the local contrast characteristics of the radiation image data of the low-energy sub-band from radiation image data generated as the radiation having at least two energy bands passes through the subject.

For example, the local contrast characteristics may be a local contrast gain, but are not limited thereto, and may include any or all parameters or factors indicating contrast characteristics of the radiation image data of the low-energy sub-band.

The local contrast gain may be calculated based on the radiation image data of the low-energy sub-band and an average value of the radiation image data of the low-energy sub-band. For example, the average value of the radiation image data of the low-energy sub-band may be filtered radiation image data obtained by passing the radiation image data of the low-energy sub-band through a low-pass filter (LPF).

Accordingly, the local contrast characteristic calculator 110 calculates the local contrast characteristics of the low-energy sub-band based on the radiation image data of the low-energy sub-band and the filtered radiation image data obtained by passing the radiation image data of the low-energy sub-band through the LPF.

For example, the LPF for generating the filtered radiation image data may be a bilateral filter, a Gaussian filter, or an averaging filter, but is not limited thereto.

In greater detail, the local contrast characteristic calculator 110 may obtain the filtered radiation image data by performing wavelet transformation, curvelet transformation, or contourlet transformation on the radiation image data of the low-energy sub-band. In other words, the local contrast characteristic calculator 110 may obtain the filtered radiation image data that has passed through the LPF by decomposing an image into a multi-scale image or a multi-direction image by performing wavelet/contourlet transformation, curvelet/contourlet transformation, or contourlet/contourlet transformation on the radiation image data of the low-energy sub-band to divide the image into low-frequency band components and high-frequency band components. The wavelet transformation, the curvelet transformation, or the contourlet transformation may also be used to calculate a local contrast gain and extract details. The wavelet transformation, the curvelet transformation, and the contourlet transformation are well known to one of ordinary skill in the art, and thus will not be described in detail herein.

Also, the local contrast characteristic calculator 110 may adjust degrees of improvement of contrast and resolution of the diagnosis image generated by the apparatus 100 by adjusting a filter size of the LPF and parameters according to a type of the LPF.

If the LPF is a Gaussian filter, since blurriness of image data increases as a standard deviation of the Gaussian filter increases, the local contrast characteristic calculator 110 may adjust the degree of improvement of resolution of the diagnosis image by adjusting the standard deviation of the Gaussian filter. The Gaussian filter is well known to one of ordinary skill in the art, and thus will not be described in further detail here.

If the LPF is a bilateral filter, a degree of blurriness may be adjusted according to an intensity level parameter of the bilateral filter. For example, since blurriness increases as the intensity level parameter of the bilateral filter decreases, a contrast of the generated diagnosis image may be improved by increasing the intensity level parameter of the bilateral filter. Also, since a size of calculated local contrast information increases as a size parameter of the bilateral filter increases, relatively large detail information may be improved by increasing the size parameter of the bilateral filter, and relatively fine detail information may be improved by decreasing the size parameter of the bilateral filter. Accordingly, the local contrast characteristic calculator 110 may perform edge-preserving by adjusting the intensity level parameter and the size parameter of the bilateral filter, thereby adjusting the degree of improvement of resolution of the diagnosis image generated by the apparatus 100. The bilateral filter is well known to one of ordinary skill in the art, and thus will not be described in further detail here.

The local contrast characteristic calculator 110 calculates the local contrast characteristics of the radiation image data of the low-energy sub-band by performing a calculation expressed by Equation 1 below.

$$c_l(x, y) = \frac{R_l(x, y)}{R_{l\_ave}(x, y)} \quad (1)$$

In Equation 1, $c_l(x,y)$ denotes a local contrast characteristic of the radiation image data of the low-energy sub-band at location coordinates (x,y) of the radiation image data, $R_l(x,y)$ denotes the radiation image data of the low-energy sub-band at the location coordinates (x,y), and $R_{l\_ave}(x,y)$ denotes the filtered radiation image data obtained by passing the radiation image data of the low-energy sub-band through the LPF at the location coordinates (x,y).

In this example, the low-energy sub-band denotes the lowest energy band of at least two energy bands of the radiation. Alternatively, the low-energy sub-band may denote an energy band below or equal to an energy level for classifying a plurality of tissues and lesions, but is not limited thereto. The low-energy sub-band will be described in detail later with reference to FIG. 5.

In FIG. 4, for convenience of description, the local contrast characteristics are calculated from the radiation image data of the low-energy sub-band on which a contrast improvement process has not been performed, but alternatively, the local contrast characteristic calculator 110 may calculate the local contrast characteristics from the radiation image data of the low-energy sub-band on which a contrast improvement process has been performed as will be described later with reference to FIG. 6.

The local contrast characteristic applier 120 applies the local contrast characteristics calculated by the local contrast characteristic calculator 110 to the radiation image data of the full-energy band that is generated as the radiation having at least two energy bands passes through the subject.

The radiation image data of the full-energy band may be the filtered radiation image data. Accordingly, the local contrast characteristic applier 120 may apply the local contrast characteristics calculated by the local contrast characteristic calculator 110 to the filtered radiation image data obtained as the radiation image data of the full-energy band passes through the LPF.

Accordingly, contrast and details of the radiation image data of the full-energy band to which the local contrast characteristics of the radiation image data of the low-energy sub-band have been applied by the local contrast characteristic applier 120 may be improved.

The local contrast characteristic applier 120 performs a calculation expressed by Equation 2 below to apply the local contrast characteristics of the radiation image data of the low-energy sub-band to the radiation image data of the full-energy band.

$$R_{f\_app}(x,y) = c_l(x,y) \cdot R_{f\_ave}(x,y) \quad (2)$$

In Equation 2, $R_{f\_app}(x,y)$ denotes the radiation image data of the full-energy band to which the local contrast characteristics have been applied at location coordinates (x,y) of the radiation image data, $R_{f\_ave}(x,y)$ denotes the filtered radiation image data obtained by passing the radiation image data of the full-energy band through the LPF at the location coordinates (x,y), and $c_l(x,y)$ denotes the local contrast characteristics of the radiation image data of the low-energy sub-band defined in Equation 1 above.

The filtered radiation image data obtained by passing the radiation image data of the full-energy band through the LPF may be generated in the same manner as the local contrast characteristic calculator 110 generates the filtered radiation image data of the radiation image data of the low-energy sub-band, which has been described above. For example, the LPF may be a bilateral filter, a Gaussian filter, or an averaging filter.

The diagnosis image generator 130 generates the diagnosis image of the subject based on the radiation image data to which the local contrast characteristics have been applied by the local contrast characteristic applier 120.

Also, the diagnosis image generator 130 may adjust the degree of improvement of resolution of the diagnosis image by applying a resolution improvement weight to the radiation image data to which the local contrast characteristics have been applied.

For example, the diagnosis image generator 130 may generate the diagnosis image based on a weighted average of the radiation image data of the full-energy band to which the local contrast characteristics have not been applied and the radiation image data of the full-energy band to which the local contrast characteristics have been applied. The radiation image data of the full-energy band to which the local contrast characteristics have not been applied may be generated from raw data obtained from the radiation radiated onto the subject by the radiation generating apparatus 300 that passes through the subject.

Accordingly, the diagnosis image generator 130 may generate the diagnosis image of the subject by performing a calculation expressed by Equation 3 below.

$$DI = R_f(1-\alpha) + R_{f\_app} \cdot \alpha \qquad (3)$$

In Equation 3, DI denotes the diagnosis image of the subject, $R_f$ denotes the radiation image data of the full-energy band to which the local contrast characteristics have not been applied, $R_{f\_app}$ denotes the radiation image data of the full-energy band to which the local contrast characteristics defined in Equation 2 above have been applied, and a denotes the resolution improvement weight.

The resolution improvement weight $\alpha$ may be a rational number from 0 to 1, and may be suitably adjusted by a user of the apparatus 100 according to the user's preference.

Accordingly, the diagnosis image generator 130 may generate the diagnosis image to have an overall improved resolution by increasing the resolution improvement weight $\alpha$, or may generate the diagnosis image to be close to the raw data by decreasing the resolution improvement weight $\alpha$.

As described above, since the apparatus 100 generates the diagnosis image based on the radiation image data to which the local contrast characteristics have been applied, a very clear diagnosis image where a difference between a dark region and a bright region is clear may be generated.

Figure 5:
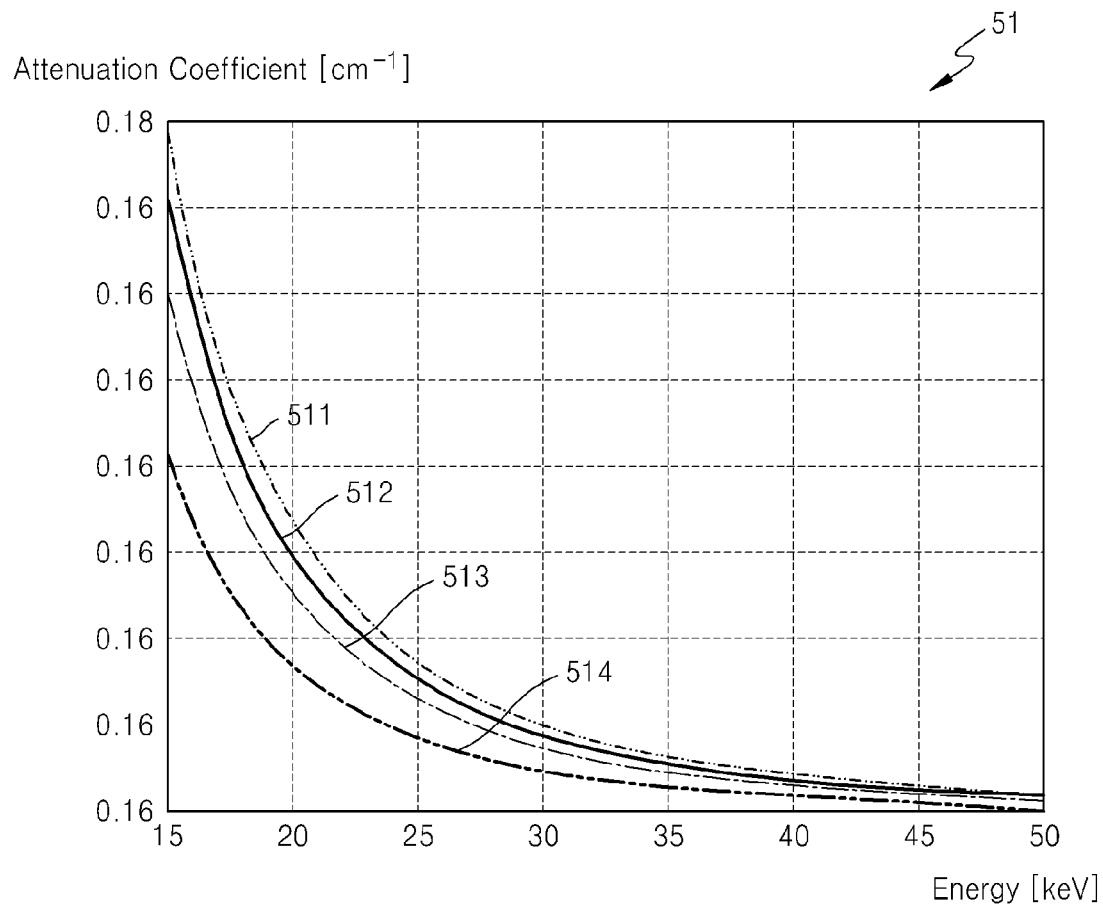
FIG. 5 is a graph showing attenuation coefficients of an x-ray with respect to energy of different tissues of a subject.

FIG. 5 is a graph 51 showing attenuation coefficients of an x-ray with respect to energy for different tissues of a subject. For convenience of description, the subject in FIG. 5 is a breast.

Referring to FIG. 5, the graph 51 shows the attenuation coefficients of an x-ray with respect to energy for different breast tissues. A breast is formed of adipose tissues, glandular tissues, and fibrous tissues. The breast may have a lesion such as a carcinoma. Examples of the carcinoma include an infiltrating ductal carcinoma (IDC) and a mass. The graph 51 shows the attenuation coefficients with respect to energy for the various types of tissues and lesions of the breast.

Referring to the graph 51, a curve 511 shows the attenuation coefficient of the fibrous tissues, a curve 512 shows the attenuation coefficient of the carcinoma, a curve 513 shows the attenuation coefficient of the glandular tissues, and a curve 514 shows the attenuation coefficient of the adipose tissues.

The attenuation coefficient of the x-ray depends on an atomic number, a density, and a number of electrons per gram of a material, and as shown in the graph 51, a difference between the attenuation coefficients of the tissues forming the breast increases as energy decreases. Thus, radiation image data of a low-energy sub-band has relatively better contrast characteristics than radiation image data of a full-energy band. Accordingly, the apparatus 100 makes use of this characteristic by generating the diagnosis image by applying the local contrast characteristics of the radiation image data of the low-energy sub-band to the radiation image data of the full-energy band.

The low-energy sub-band may be below or equal to 30 keV, but is not limited thereto, and may be an energy band below or equal to an energy level for classifying a plurality of tissues forming the subject and lesions.

Figure 6:
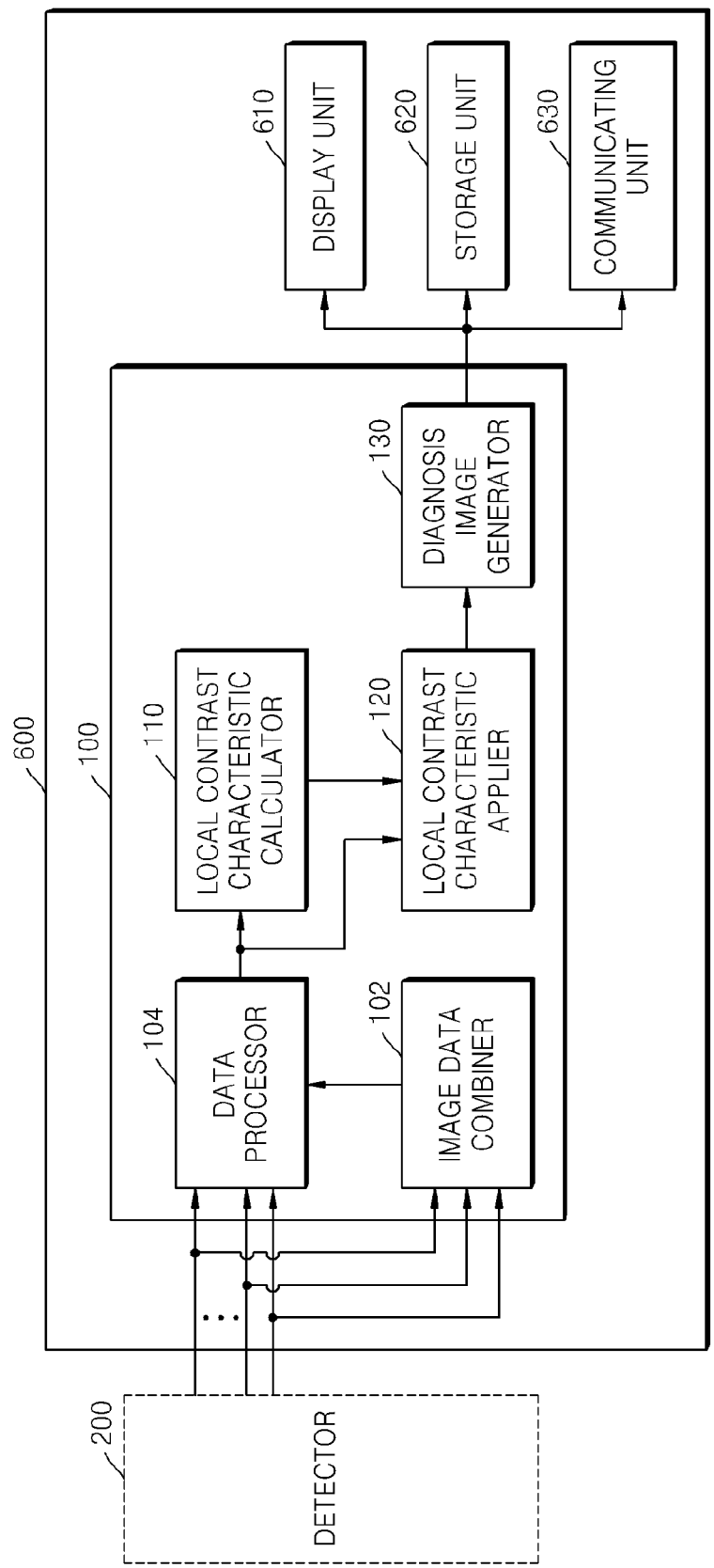
FIG. 6 is a block diagram of a medical imaging system according to an example.

FIG. 6 is a block diagram of a medical imaging system 600 according to an example. Referring to FIG. 6, the medical imaging system 600 includes the apparatus 100, a display unit 610, a storage unit 620, and a communicating unit 630. The apparatus 100 includes an image data combiner 102, a data processor 104, the local contrast characteristic calculator 110, the local contrast characteristic applier 120, and the diagnosis image generator 130.

The apparatus 100 of FIG. 6 corresponds to the apparatus 100 of FIG. 4. However, the elements of the apparatus 100 are not limited to those shown in FIG. 6. Also, since descriptions of FIGS. 1 through 5 are also applicable to the apparatus 100 of FIG. 6, the descriptions of FIGS. 1 through 5 will not be repeated here.

Only elements relevant to this example are shown in the medical imaging system 600 of FIG. 6. However, it will be apparent to one of ordinary skill in the art that other elements may also be included in the medical imaging system 600.

Examples of the medical imaging system 600 include all image diagnosing systems using radiation, for example, x-rays. For example, the medical imaging system 600 may be a mammography image diagnosing system used to detect a lesion of breast tissue, which is formed only of soft tissue, in a human body.

The apparatus 100 generates the diagnosis image of the subject by applying the local contrast characteristics of the radiation image data of the low-energy sub-band to the radiation image data of the full-energy band.

The image data combiner 102 combines a plurality of pieces of radiation image data generated by the detector 200. The radiation image data generated by the detector 200 may be radiation image data of each of at least two energy bands of the radiation. For example, the detector 200 may generate three pieces of radiation image data of three energy bands.

For example, the image data combiner 102 may generate the radiation image data of the full-energy band by applying a weighted summation method to the radiation image data of each of the at least two energy bands.

Alternatively, the detector 200 may generate the radiation image data of the full-energy band, and in this case, the image data combiner 102 of FIG. 6 need not operate.

The data processor 104 performs at least one predetermined process on at least one of the radiation image data generated by the detector 200 and the radiation image data combined by the image data combiner 102. For example, the data processor 104 may perform a noise reduction process, or a contrast improvement process, or a detail improvement process, or any combination thereof.

If the data processor 104 performs the contrast improvement process, the data processor 104 may perform the contrast improvement process by dividing the radiation image data generated by the detector 200 into a plurality of regions according to brightness levels, and applying contrast stretching to each of the regions.

The data processor 104 may perform the contrast improvement process on the radiation image data of each of the at least two energy bands.

In greater detail, the data processor 104 may perform the contrast improvement process on the radiation image data of the low-energy sub-band, and the local contrast characteristic applier 120 may perform the contrast improvement process on the radiation image data of the full-energy band.

Alternatively, the data processor 104 may perform the contrast improvement process on the radiation image data of the full-energy band, and the local contrast characteristic applier 120 may again perform the contrast improvement process on the radiation image data of the full-energy band.

The data processor 104 may divide the radiation image data generated by the detector 200 into regions based on the brightness levels for classifying each of the tissues forming the subject. If the subject is a breast, the data processor 104 may divide the radiation image data into regions based on the brightness levels for classifying each of adipose tissues, glandular tissues, a carcinoma, and fibrous tissues.

Alternatively, the data processor 104 may divide the radiation image data into regions, and perform the contrast improvement process on each of the regions by using different contrast stretching techniques.

For example, the data processor 104 may divide the radiation image data into regions based on a reference point, and perform contrast stretching by using different techniques on radiation image data having a brightness level below the reference point and radiation image data having a brightness level equal to or above the reference point.

Accordingly, the data processor 104 may perform the contrast improvement process on the radiation image data by performing a calculation expressed by Equation 4 below.

$$R_n = \begin{cases} \dfrac{x - P_n}{P_{n+1} - P_n}, & \text{if } x < P_{n+1} \\ \dfrac{P_{n+1} - x}{1 - P_{n+1}}, & \text{if } x \geq P_{n+1} \end{cases} \quad (4)$$

In Equation 4, x denotes the brightness level of the radiation image data generated by the detector 200, $R_n$ denotes the brightness level of the radiation image data on which the contrast improvement process has been performed, $P_n$ denotes the brightness level of the reference point, and n denotes a number of the reference point, where n is an integer equal to or above 0.

For example, where brightness levels of pixels of the radiation image data are normalized to 1, $P_0$ may be 0 and $P_n$ may be 1.

Accordingly, when the data processor 104 performs the contrast improvement process, a dark region of the radiation image is brightened and a bright region of the radiation image is darkened. Also, since the data processor 104 applies different contrast stretching techniques to the regions based on the reference point, an effect of the contrast stretching may be improved.

The local contrast characteristic calculator 110 calculates the local contrast characteristics of the radiation image data of the low-energy sub-band from radiation image data generated as the radiation having at least two energy bands passes through the subject, the local contrast characteristic applier 120 applies the calculated local contrast characteristics to the radiation image data of the full-energy band, and the diagnosis image generator 130 generates the diagnosis image of the subject based on the radiation image data to which the local contrast characteristics have been applied.

The display unit 610 displays the diagnosis image generated by the diagnosis image generator 130. Examples of the display unit 610 include all output devices, such as a display panel, a liquid crystal display (LCD) screen, and a monitor, installed in the medical imaging system 600.

However, instead of the display unit 610, the medical imaging system 600 may use the communicating unit 630 to output the diagnosis image generated by the diagnosis image generator 130 to an external display device (not shown).

The storage unit 620 stores data generated while the medical imaging system 600 is operating. The storage unit 620 is a general storage medium, and examples of the storage unit 620 include a hard disk drive (HDD), a read only memory (ROM), a random access memory (RAM), a flash memory, a memory card, and any other type of storage device that is known in the art and is capable of storing the data generated while the medical imaging system 600 is operating.

The communicating unit 630 transmits and receives data to and from an external device via a wired or wireless network, or a wired series communication. Examples of a network include the Internet, a local area network (LAN), a wireless LAN, a wide area network (WAN), and a personal area network (PAN), but are not limited thereto as long as the network is capable of transmitting and receiving information.

The storage unit 620 and the communicating unit 630 may be integrated into a picture archiving and communication system (PACS) that further includes image reading and seeking functions.

Accordingly, the medical imaging system 600 may display, store, and output a high definition diagnosis image generated by applying the local contrast characteristics of the radiation image data of the low-energy sub-band, which has relatively excellent contrast and detail characteristics, to the radiation image data of the full-energy band, which has relatively excellent noise characteristics. Accordingly, a medical expert using the medical imaging system 600 may easily detect and diagnose an existence, size, and location of a lesion.

Figure 7:
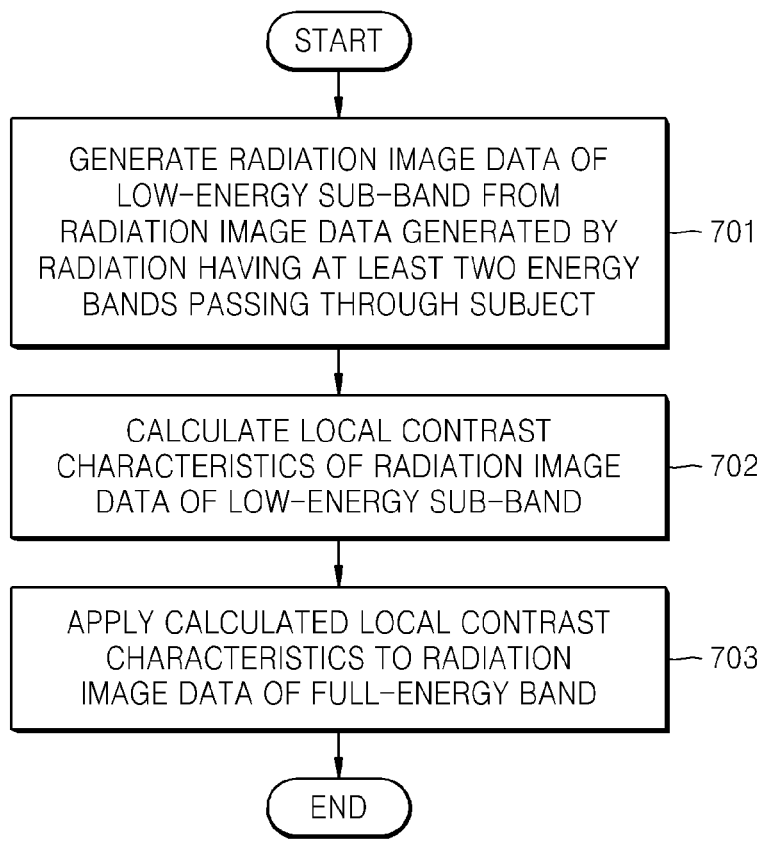
FIG. 7 is a flowchart illustrating a method of processing an image according to an example.

FIG. 7 is a flowchart illustrating a method of processing an image according to an example. Referring to FIG. 7, the method includes operations performed in time series by the radiation image capturing system 10, the apparatus 100, and the medical imaging system 600 of FIGS. 1, 4, and 6. Accordingly, the descriptions of the radiation image capturing system 10, the apparatus 100, and the medical imaging system 600 of FIGS. 1, 4, and 6 are also applicable to the method of FIG. 7, but will not be repeated here for conciseness.

In operation 701, the detector 200 generates radiation image data of a low-energy sub-band from radiation image data generated by radiation having at least two energy bands passing through a subject.

In operation 702, the local contrast characteristic calculator 110 uses at least one processor to calculate the local contrast characteristics of the radiation image data of the low-energy sub-band generated in operation 701. For example, the local contrast characteristics may be a local contrast gain.

In operation 703, the local contrast characteristic applier 120 applies the local contrast characteristics calculated in operation 702 to the radiation image data of the full-energy band.

Since the local contrast characteristics of the radiation image data of the low-energy sub-band, which has relatively excellent contrast characteristics, are applied to the radiation image data of the full-energy band, a very clear diagnosis image may be obtained.

As described above, according to one or more of the above examples, a high definition diagnosis image can be obtained. Accordingly, medical experts can accurately determine whether a lesion exists, as well as its size and location, in a subject.

The apparatus 100 for generating a diagnosis image in FIGS. 1, 4, and 6; the local contrast characteristic calculator 110, the local contrast characteristic applier 120, and the diagnosis image generator in FIGS. 4 and 6; and the image data combiner 102 and the data processor 104 in FIG. 6 may be implemented using hardware components and/or software components. Software components may be implemented by a processing device, which may be implemented using one or more general-purpose or special-purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purposes of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

As used herein, a processing device configured to implement a function A includes a processor programmed to run specific software. In addition, a processing device configured to implement a function A, a function B, and a function C may include configurations, such as, for example, a processor configured to implement functions A, B, and C; a first processor configured to implement function A and a second processor configured to implement functions B and C; a first processor configured to implement functions A and B and a second processor configured to implement function C; a first processor to implement function A, a second processor configured to implement function B, and a third processor configured to implement function C; a first processor configured to implement functions A, B, C and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion.

In particular, the software and data may be stored by one or more non-transitory computer-readable storage mediums. The non-transitory computer-readable storage medium may include any data storage device that can store data that can be thereafter read by a computer system or processing device. Examples of a non-transitory computer-readable storage medium include read-only memory (ROM), random-access memory (RAM), CD-ROMs, magnetic tapes, floppy disks, and optical data storage devices. Also, functional programs, codes, and code segments for implementing the examples disclosed herein can be easily constructed by programmers skilled in the art to which the examples pertain based on the drawings and their corresponding descriptions as provided herein.

While this disclosure has been particularly shown and described with reference to examples thereof, it will be understood by those skilled in the art that various changes in form and details may be made in these examples without departing from the spirit and scope of the invention as defined by the claims and their equivalents. It should be understood that the examples described herein should be considered in a descriptive sense only, and not for purposes of limitation. Descriptions of features or aspects in each example are to be considered as being applicable to similar features or aspects in other examples. Suitable results may be achieved if the described techniques are performed in a different order and/or if components in a described system, architecture, device, or circuit are combined in a different manner and/or replaced or supplemented by other components or their equivalents. Therefore, the scope of the invention is defined not by the detailed description of the disclosure, but by the claims and their equivalents, and all variations within the scope of the claims and their equivalents are to be construed as being included in the invention.

What is claimed is:

1. An apparatus for generating a diagnosis image, the apparatus comprising:
    a local contrast characteristic calculator configured to calculate local contrast characteristics of radiation image data of a low-energy sub-band from radiation image data generated by passing radiation having at least two energy bands through a subject, wherein the local contrast characteristics are a local contrast gain of the radiation image data of the low energy sub-band;
    a local contrast characteristic applier configured to apply the calculated local contrast characteristics to radiation image data of a full-energy band generated by passing the radiation having at least two energy bands through the subject, the radiation image data of a full-energy band comprising the radiation image data of the low-energy sub-band; and
    a diagnosis image generator configured to generate a diagnosis image of the subject based on the radiation image data of the full-energy band to which the calculated local contrast characteristics have been applied.

2. The apparatus of claim 1, wherein the local contrast characteristic calculator is further configured to calculate the local contrast characteristics based on the radiation image data of the low-energy sub-band and filtered radiation image data obtained by passing the radiation image data of the low-energy sub-band through a low-pass filter (LPF).

3. The apparatus of claim 2, wherein the local contrast characteristic calculator is further configured to adjust a resolution improvement degree of the diagnosis image generated by the diagnosis image generator by adjusting parameters of the LPF.

4. The apparatus of claim 3, wherein the passing of the radiation image data of the low-energy sub-band through the LPF to obtain the filtered radiation image data comprises passing the radiation image data of the low-energy sub-band through a bilateral filter, or a Gaussian filter, or an averaging filter, or performing wavelet transformation, or curvelet transformation, or contourlet transformation on the radiation image data of the low-energy sub-band.

5. The apparatus of claim 3, wherein the passing of the radiation image data of the low-energy sub-band through the LPF to obtain the filtered radiation image data comprises passing the radiation image data of the low-energy sub-band through a Gaussian filter or a bilateral filter; and
the local contrast characteristic calculator is further configured to adjust a contrast improvement degree of the diagnosis image generated by the diagnosis image generator by adjusting a standard deviation of the Gaussian filter or an intensity level parameter of the bilateral filter.

6. The apparatus of claim 1, wherein the local contrast characteristic applier is further configured to apply the calculated local contrast characteristics to filtered radiation image data obtained by passing the radiation image data of the full-energy band through a low-pass filter (LPF).

7. The apparatus of claim 6, wherein the LPF is a bilateral filter, or a Gaussian filter, or an averaging filter.

8. The apparatus of claim 1, wherein the diagnosis image generator is further configured to adjust a resolution improvement degree of the diagnosis image by combining the radiation image data of the full-energy band to which the calculated local contrast characteristics have not been applied with the radiation image data of the full-energy band to which the calculated local contrast characteristics have been applied according to a resolution improvement weight.

9. The apparatus of claim 1, further comprising a data processor configured to:
divide the radiation image data of the low-energy sub-band into a plurality of brightness regions based on a brightness reference point; and
perform contrast stretching on the radiation image data of the low-energy sub-band by performing a first contrast stretching technique on radiation image data of the low-energy sub-band having a brightness level below the brightness reference point, and performing a second contrast stretching technique different from the first contrast stretching technique on radiation image data of the low-energy sub-band having a brightness level equal to or above the brightness reference point;
wherein the local contrast characteristic calculator is further configured to calculate the local contrast characteristics based on the radiation image data of the low-energy sub-band on which the contrast stretching has been performed.

10. A medical imaging system comprising:
an apparatus configured to generate a diagnosis image of a subject by applying local contrast characteristics of radiation image data of a low-energy sub-band to radiation image data of a full-energy band, the radiation image data of the low-energy sub-band and the radiation image data of the full-energy band having been generated by passing radiation through the subject, wherein the local contrast characteristics are a local contrast gain of the radiation image data of the low-energy sub-band; and
a display unit configured to display the generated diagnosis image.

11. The medical imaging system of claim 10, wherein the apparatus is further configured to calculate the local contrast characteristics based on the radiation image data of the low-energy sub-band and filtered radiation image data obtained by passing the radiation image data of the low-energy sub-band through a low-pass filter (LPF).

12. A method of processing an image, the method comprising:
generating radiation image data of a low-energy sub-band from radiation image data generated by passing radiation having at least two energy bands through a subject;
calculating local contrast characteristics of the generated radiation image data of the low energy sub-band, wherein the local contrast characteristics are a local contrast gain of the radiation image data of the low-energy sub-band; and
applying the calculated local contrast characteristics to radiation image data of a full energy band.

13. The method of claim 12, wherein the calculating of the local contrast characteristics comprises calculating the local contrast characteristics based on the radiation image data of the low-energy sub-band and filtered radiation data obtained by passing the radiation image data of the low-energy sub-band through a low-pass filter (LPF).

14. The method of claim 13, wherein the LPF is a bilateral filter, or a Gaussian filter, or an averaging filter.

15. The method of claim 12, further comprising:
dividing the radiation image data of the low-energy sub-band into a plurality of brightness regions based on a brightness reference point; and
performing contrast stretching on the radiation image data of the low-energy sub-band by performing a first contrast stretching technique on radiation image data of the low-energy sub-band having a brightness level lower than the brightness reference point, and performing a second contrast stretching technique different from the first contrast stretching technique on radiation image data of the low-energy sub-band having a brightness level equal to or above the brightness reference point;
wherein the calculating of the local contrast characteristics comprises calculating the local contrast characteristics based on the radiation image data of the low-energy sub-band on which the contrast stretching has been performed.

16. The method of claim 12, further comprising generating a diagnosis image of the subject by combining the radiation image data of the full-energy band to which the calculated local contrast characteristics have not been applied with the radiation image data of the full-energy band to which the local contrast characteristics have been applied according to a resolution improvement weight.

17. A non-transitory computer-readable storage medium storing program instructions for controlling one or more processors to perform the method of claim 12.

18. An apparatus for generating a diagnosis image, the apparatus comprising: a local contrast characteristic calculator configured to calculate local contrast characteristics of radiation image data of a first energy band from radiation image data that was generated by passing radiation through a subject, wherein the local contrast characteristics are a local contrast gain of the radiation image data of the first energy band;
a local contrast characteristic applier configured to apply the calculated local contrast characteristics to radiation image data of a second energy band wider than the first energy band that was generated by passing the radiation through the subject; and
a diagnosis image generator configured generate a diagnosis image of the subject based on the radiation image data of the second energy band to which the local contrast characteristics have been applied.

19. The apparatus of claim 18, wherein the first energy band comprises energies not exceeding a predetermined energy; and the second energy band comprises the first energy band and energies above the predetermined energy, and does not comprise any energy lower than a lowest energy of the first energy band.

20. The apparatus of claim 18, wherein the first energy band is a lowest energy band of the radiation that has passed through the subject;

the second energy band comprises the first energy band; and the radiation that has passed through the subject comprises radiation in a third energy band comprising the second energy band.

* * * * *